(12) United States Patent
Pascal et al.

(10) Patent No.: US 7,067,623 B2
(45) Date of Patent: Jun. 27, 2006

(54) VOLATILIZABLE SOLID PHASE SUPPORTS FOR COMPOUND SYNTHESIS

(75) Inventors: Jeanick H. Pascal, San Diego, CA (US); Michael J. Moran, San Diego, CA (US); Richard A. Houghten, DelMar, CA (US)

(73) Assignee: Mixture Sciences, Inc., San Diego, CA (US)

( * ) Notice: Subject to any disclaimer, the term of this patent is extended or adjusted under 35 U.S.C. 154(b) by 284 days.

(21) Appl. No.: 10/286,670

(22) Filed: Nov. 1, 2002

(65) Prior Publication Data

US 2003/0135024 A1 Jul. 17, 2003

Related U.S. Application Data

(62) Division of application No. 09/493,902, filed on Jan. 28, 2000, now Pat. No. 6,476,191.

(60) Provisional application No. 60/119,204, filed on Feb. 5, 1999.

(51) Int. Cl.
*C07K 1/04* (2006.01)

(52) U.S. Cl. .................. 530/334; 530/333; 435/72

(58) Field of Classification Search .............. 435/72; 530/333, 334
See application file for complete search history.

(56) References Cited

U.S. PATENT DOCUMENTS

| | | | |
|---|---|---|---|
| 3,901,872 A | 8/1975 | McKinley et al. | 260/112.5 |
| 4,623,716 A * | 11/1986 | Stevenson et al. | 530/333 |
| 4,631,270 A * | 12/1986 | Yankeelov et al. | 514/15 |
| 5,037,882 A | 8/1991 | Steel | 525/54.11 |
| 5,188,733 A | 2/1993 | Wang et al. | 210/321.84 |
| 5,369,017 A | 11/1994 | Wong et al. | 435/68.1 |
| 5,455,227 A | 10/1995 | Curstedt et al. | 514/14 |
| 5,513,024 A | 4/1996 | Kang | 359/62 |
| 5,552,471 A | 9/1996 | Woo et al. | 524/494 |
| 5,859,277 A | 1/1999 | Whitlock et al. | 556/400 |
| 5,922,840 A | 7/1999 | Tomich et al. | 530/344 |
| 6,008,321 A | 12/1999 | Li et al. | 530/334 |

FOREIGN PATENT DOCUMENTS

| | | |
|---|---|---|
| WO | WO 98/22197 | 5/1998 |
| WO | WO 00/46238 | 8/2000 |

OTHER PUBLICATIONS

Zheng, J. Org. Chem. 63, 1126-30, 1998.*
Seeberger, Peter H., Journal of Carbohydrate Chemistry (2002), 21(7-9), 613-643.*
Seeberger, P. H., J. Am. Chem. Soc. 1997; 119(42): 10064-10072.*
Seeberger P. H., Acc. Chem. Res. 31, 685-695 1998.*
Merrifield, J. Am. Chem. Soc., 85:2149-2154 (1963).
Atherton, et al., J. Am. Chem. Soc., 97:6584-6585 (1975).
Parr, et al., Liebigs Ann. Chem., pp. 655-666 (1974).
Fodor, et al., Science, 251:767-773 (1991).
Plunkett, et al., J. Org. Chem., 60:6006-6007 (1995).
Houghten, et al., Proc. Natl. Acad. Sci. USA, 82:5131-5135 (1985).
Houghten, et al., Nature, 354:84-86 (1991).
Pinella, et al., BioTechniques, 13:901-905 (1992).
Ostresh, et al., Proc. Natl. Acad. Sci. USA, 91:11138-11142 (1994).
Dooley, et al., Science, 266:2019-2022 (1994).
Eichler, et al., Molecular Medicine Today, 1:174-180 (1995).
Atherton, et al., Perspectives in Peptide Chemistry, pp. 101-117 (1981).
Bayer, et al., Tetrahedron Letters, 51:4503-4505 (1970).
Parr, et al., Angew. Chem. Internat. Edit., 11:314-315 (1972).
Danishefsky, et al., Science, 260:1307-1309 (1993).
Wong, et al., J. Am. Chem. Soc., 115:5893:5901 (1993).
Bianco, et al., J. Am. Chem. Soc., 119:7550-7554 (1997).

* cited by examiner

*Primary Examiner*—David Lukton
(74) *Attorney, Agent, or Firm*—Welsh & Katz, Ltd.

(57) ABSTRACT

A solid phase synthetic method is disclosed in which the usual solid phase synthetic steps are carried out and the spent solid phase support is reacted to form a volatilizable compound upon cleavage of the reaction product from the solid phase support. The cleaved product is then separated from the volatile compound by volatilization of that compound. Exemplary solid supports that form a volatilizable compound are also disclosed.

8 Claims, No Drawings

VOLATILIZABLE SOLID PHASE SUPPORTS FOR COMPOUND SYNTHESIS

CROSS-REFERENCE TO RELATED APPLICATION

This is a division of application Ser. No. 09/493,902, filed Jan. 28, 2000, now U.S. Pat. No. 6,476,191, which claimed priority from application Ser. No. 60/119,204 filed Feb. 5, 1999, whose disclosures are incorporated herein by reference.

TECHNICAL FIELD

The invention relates to solid phase syntheses, and more particularly to solid phase synthesis on a synthetic support that is volatilized upon the cleavage of the synthesized material from the support.

BACKGROUND OF THE INVENTION

The preparation of compounds using a solid phase approach was first described by Merrifield in 1963 [Merrifield, 1963, *J. Am. Chem. Soc.*, 85:2149–2154. Since this initial seminal concept, in which a polystyrene solid phase was used to prepare peptides, a wide range of different solid supports have been used (i.e., polyamides [Atherton et al., 1975, *J. Am. Chem. Soc.*, 97:6584–6585], porous glass [Parr et al., 1974. *Justus Liebigs Ann. Chem.*, pp. 655–666] and microchip quartz [Fodor et al., 1991, *Science*, 251:767–773]). While useful, these solid phase supports all require a final cleavage step, in which the compounds (peptides, peptidomimetics, oligonucleotides, small organic molecules, various heterocycles, and the like) are cleaved from the solid phase, then separated from the spent solid support.

Where the compound of interest can be used in an immobilized manner (i.e., it remains on the solid support in its final use and/or manifestation), then the remaining solid support may not be problematic, and in fact may be useful for certain assays. However, in the majority of cases, the compound of interest has to be used in solution and therefore has to be separated from its solid support. Significant time and/or cost savings would be realized if the removal of the solid phase material did not have to be accomplished in a separate step following cleavage of the desired compound from the solid support (typically by filtration or centrifugation). The invention disclosed hereinafter provides one solution to the problem of separating the spent solid support from the desired synthesized material.

BRIEF SUMMARY OF THE INVENTION

The present invention contemplates solid phase synthesis on a solid support in which the desired product is left behind following cleavage from and vaporization of the solid. Thus, a solid phase synthesis method is contemplated in which at least one reagent is coupled to a solid phase support. A plurality of reactions is carried out upon the solid phase-coupled reagent to form a solid phase-coupled reaction product, and the reaction product is cleaved from the solid phase support to form a cleaved product. The improvement in this otherwise standard synthesis is that the solid phase support is reacted to form a volatile compound(s) that is separated from the cleaved product by vaporization as by distillation. The desired cleaved product is preferably recovered and the solid support is absent due to its volatilization.

A particularly preferred solid support is silica. Cleavage of the product from the solid support and formation of the volatile compound is typically carried out in a single step, although separate steps can be used.

The present invention has several benefits and advantages.

One benefit is the simplicity in reaction steps that are carried out in that the usual filtering step required in prior solid phase syntheses is not required.

An advantage of a contemplated method is that losses of desired product that can occur because of entrapment of the desired product within the usual spent solid support or filter do not occur.

Another benefit is that the usual final extraction step(s) to remove the product from the solid support required in prior solid phase syntheses after cleavage from the solid support is not required here.

Still further benefits and advantages of the contemplated invention will be apparent to the skilled worker from the disclosure that follows.

DETAILED DESCRIPTION OF THE INVENTION

A solid phase synthetic method is contemplated in which the usual solid phase synthetic steps are carried out in the synthesis of a peptide, peptidomimetic, glycopeptide, oligonucleotide, small organic molecules, or heterocyclic product as noted hereinafter. The improvement here lies in the separation of the cleaved product from the solid support by conversion of the solid phase support into a volatile material that is separated from the desired reaction product by vaporization so that the usually used filtration or extraction separation of the desired product from the spent solid phase support is unnecessary.

Thus, taking a solid phase peptide synthesis as exemplary, at least one reagent such as a side chain- and N-protected amino acid is coupled to the solid support. A plurality of reactions is carried out on that solid phase-coupled reagent such as N-de-protection, coupling of another side chain- and N-protected amino acid, and N-de-protecting the resulting product to form a solid phase-coupled reaction product. Any side chain protecting groups present are removed, and the link between solid support and desired product is broken to form a cleaved product. A volatile compound is formed from the spent solid support. In preferred practice for peptide synthesis, HF is used to remove any side chain protecting groups present, cleave the product from the solid support and form the volatile compound(s) from the spent solid support.

As used herein, the material formed on the solid phase support and bonded thereto is referred to as a "reaction product". The reaction product can have protecting groups bonded to it or those protecting groups can be removed.

The "cleaved product" is that material obtained upon breaking of the bond between the solid phase support and the reaction product. The cleaved product is typically free of protecting groups but need not be so. In addition, the cleaved product is typically protonated, although protonation is not a defining feature of a cleaved product.

A "spent solid support" is the material remaining after cleavage of the desired reaction product from the support. As discussed below, the solid support is preferably converted into a volatile compound concomitantly with formation of the cleaved product. In that preferred case, there is usually no spent solid support.

For example, porous glass has been used as a solid support to prepare a peptide with cleavage of the desired product effected by reaction of the solid phase-bound peptide with methanol and triethylamine. [Parr et al., 1974, *Justus Liebigs Ann. Chem.*, pp. 655–666.] Contrarily, using a contemplated method, the porous glass can be completely transformed by liquid or gaseous hydrogen fluoride into volatile silicon tetrafluoride ($SiF_4$, bp: −86° C.) that can be warmed or a vacuum applied to effect separation, as compared to use of a reagent that cleaves the compound from the support followed by filtration of the spent solid support from the desired compound as was carried out by Parr et al. Use of a contemplated method leaves the desired compound in the reaction container, with the porous glass solid support volatilized away as $SiF_4$.

This concept greatly facilitates the production of individual compounds or mixtures of compounds, or the large scale production of individual compounds, arrays of compounds, or combinatorial libraries of mixtures [Plunkett et al., 1995, *J. Org. Chem.*, 60:6006–6007; Houghten, 1985, *Proc. Natl. Acad. Sci. USA*, 82:5131–5135; Houghten et al., 1991, *Nature*, 354:84–86; Pinilla et al., 1992, *BioTechniques* 13: 901–905; Ostresh et al., 1994, *Proc. Natl. Acad. Sci. USA*, 91: 11138–11142; Dooley et al., 1994, *Science*, 266: 2019–2022; and Eichler et al., 1995, *Molecular Medicine Today* 1:174–180]. In addition, when working with mixtures of compounds, the risk of losing part of the compounds during the separation process of the solid phase (filtration or centrifugation) is minimized.

The present invention also contemplates the use of so-called non-cleavable linkers in connection with such volatilizable solid supports. A non-cleavable linker is a linker that remains bonded to the cleaved product, but is cleaved from the support. This use leads, after cleavage, to a modified compound (compound attached to linker) that can be of interest in itself, or that can be further modified if necessary.

Exemplary non-cleavable linkers can be prepared using amino-$C_2$–$C_6$-alkyl-grafted glass beads as a solid support to prepare a compound such as a peptide. Exemplary aminopropyl glass beads having different pore sizes, mesh sizes and micromoles of primary amine per gram of glass (μmol/g) are commercially available from Sigma Chemical Co., St. Louis, Mo., as is aminopropyl silica gel that is said to contain nitrogen at 1–2 mmoles/g.

Thus, use of aminopropyl-grafted glass beads to form the solid support linked peptide, followed by treatment with HF provides a peptide with a C-terminal trifluorosilylpropylamido (—CO—NH—$CH_2$—$CH_2$—$CH_2$—$SiF_3$) group that can be readily hydrolyzed to form the corresponding silicic acid group [—CO—NH—$CH_2$—$CH_2$—$CH_2$—$Si(OH)_3$]. This compound, after partial or complete polymerization through the —$Si(OH)_3$ group, can be used as a conjugate for immunization in the preparation of antibodies against the peptide of interest. Furthermore, such materials can be useful for the affinity purification of polyclonal antibodies generated against the peptide or the compound of interest. The silicon atom can also be present after such hydrolyses as a —$Si(OH)_2F$ or —$Si(OH)F_2$ group, which can also be used in a polymerization or other reaction.

In addition to an aminopropyl group, other linking groups are also contemplated. For example, 3-mercaptopropyltrimethoxysilane [HS—$CH_2$—$CH_2$—$CH_2$—$Si(OCH_3)_3$] available from Huls America, Inc., Piscataway, N.J. can be coupled to porous glass beads to provide 3-mercaptopropyl-grafted glass (thiolated glass). Reaction of the thiolated glass with bis-N-BOC-2-aminoethyl disulfide provides a primary amine-terminated disulfide after deprotection. The primary amine can be used to synthesize peptides in a usual solid phase synthesis. Upon completion of the synthesis, treatment of the reaction product-linked glass with a reducing agent and then HF provides a peptide having a C-terminal amidoethylmercapto group and a vaporizable remnant of the solid support. The amidoethylmercapto-terminated peptide can be readily reacted with an antigenic carrier molecule previously reacted with m-maleimidobenzoyl-N-hydoxysuccinimide ester (ICN Biochemicals, Inc., Costa Mesa, Calif.) or succinimidyl 4-(N-maleimidomethyl)cyclohexane-1-carboxylate (SMCC, Pierce Chemical Co., Rockford, Ill.) to form an immunogenic conjugate.

The disulfide-containing BOC-protected linking group precursor can be prepared by standard techniques. For example, 2-aminoethyl disulfide can be reacted with two moles of 2-(tert-butoxycarbonyl-oxylmino)-2-phenylacetonitrile or N-(tert-butoxy-carbonyloxy)phthalimide or a similar reagent to form bis-N-BOC-2-aminoethyl disulfide.

Several reducing reagents are well known to be useful for breaking the disulfide bond. Exemplary reagents include sodium borohydride, 2-mercapto-ethanol, 2-mercaptoethylamine, dithiothreitol and dithioerythritol. Mercaptan-containing carboxylic acids having two to three carbon atoms and their alkali metal and ammonium salts are also useful. Those reagents include thioglycolic acid, thiolactic acid and 3-mercaptopropionic acid. Exemplary salts include sodium thioglycolate, potassium thiolactate, ammonium 3-mercaptopropionate and (2-hydroxyethyl)-ammonium thioglycolate.

The use of cleavable linking groups that separate both from the cleaved product and from the solid support is also contemplated. One group of cleavable linkers contains a benzyl group and silicon. Upon treatment with specific reagents, such cleavable linkers can be transformed into gases or liquid forms that can be readily volatilized at various useful temperatures and pressures. Such linking groups are thus cleavable and form volatile compound(s) on reaction of HF with the solid support.

For example, linkers such as Cl—$CH_2C_6H_4$—$(CH_2)_{3-5}$—$SiCl_3$, Cl—$CH_2C_6H_4$—$(CH_2)_{3-5}$—$Si(CH_3)Cl_2$, Cl—$CH_2C_6H_4$—$(CH_2)_{3-5}$—$Si(CH_3)_2Cl$, Cl—$CH_2C_6H_4$—$SiCl_3$ and Cl—$CH_2$—$C_6H_4$—$Si(OCH_3)_3$ can be reacted with glass beads (or any $SiO_2$ based material) to form α-chlorobenzyl $C_3$–$C_5$-alkyl-grafted glass beads or α-chlorobenzyl-grafted glass beads, respectively, that contain one or more siloxane bonds with the support. Exemplary α-cholorbenzyl $C_3$–$C_5$-alkyl chlorosilanes and α-chlorobenzyl chloro- or methoxysilanes are avaliable from Huls America, Inc., Piscataway, N.J. This grafted glass support can then be reacted through the chloromethyl group with a wide variety of compounds such as protected amino acids, amines, alcohols, and the like to form benzyl ether groups. In the case where n=1 and one methylene group is present between the ring and silicon atom, this linker can be transformed into the volatile para (trifluorosilylmethyl)benzyl fluoride (F—$CH_2C_6H_4$—$CH_2$—$SiF_3$) by treatment with gaseous or liquid hydrogen fluoride.

Although porous glass or other silica-based solid supports are used as examples here, it is contemplated that a wide range of polymeric and/or other solid materials can be used in a similar manner. Thus, the desired solid-phase synthesized compounds are cleaved from their solid phase, while the spent solid support is completely degraded to volatile by products yielding a clear simplification of the overall synthesis process.

As one of many examples, the present invention contemplates use of solid phase polymers such as the poly(benzyl ether) shown in Formula A in which n is one to greater than 100,000 and X is the reaction product linked to the support by ester, amide, urethane, urea, amine or other bond, or a similar polymer containing a cross-linking agent such as 1,3,5-trihydroxymethylbenzene.

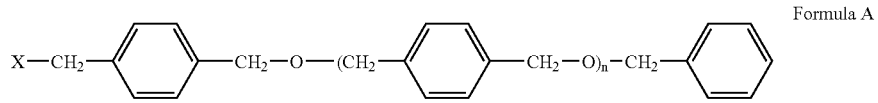

Formula A

Upon cleavage with a strong acid or a range of reducing agents such as hydrogen in the presence of palladium acetate or palladium metal hydrogenation catalyst, not only is the bond between the polymer and the desired compound X cleaved, but also are the bonds that make up the solid phase polymer itself. Use of hydrogen fluoride as the cleavage agent, provides the volatile compound shown in Formula B as the primary product.

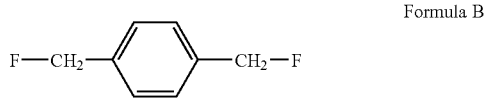

Formula B

A contemplated poly(benzyl ether) can be prepared by well-known techniques. For example, 1,4-benzenedimethanol and a suitable strong base such as t-butoxide are reacted with a dihalotoluene such as a,a'-dichloro-p-xylene in an appropriate solvent such as ethylene glycol diethyl or dimethyl ether. The cross-linker is present at zero to about 10 weight percent, and more preferably at about 1 to about 5 weight percent. After polymerization, halomethyl groups can be added to the phenyl rings to provide further places for linkage of the reaction product. For example, chloromethyl groups can be added chloromethylated by reaction of the polymer with chloromethyl methyl ether in the presence of aluminum chloride or similar Friedel-Crafts catalyst.

As noted previously, it is preferred that the reaction product be cleaved from the solid support in a single step. Where hydrogen fluoride is used along with a porous silica support in peptide synthesis, for example, the addition of HF to a side chain protected support-linked peptide can effect deprotection, cleavage of the peptide from the support and conversion of the spent silica support into the volatile compound $SiF_4$ all in one step, although several different reactions are carried out in that one step. It is also contemplated that side chain deprotection be carried out separately, as where trifluoroacteic acid is used for that reaction. It is also contemplated that cleavage of the reaction product from the support be carried out as a separate step as by the use of triethylamine and methanol, followed by reaction with HF to form the cleaved product peptide and $SiF_4$ that is then removed by volatilization.

The cleaved product is preferably recovered directly, but is usually purified chromatographically prior to further use. However, it is also contemplated that the cleaved product can be further reacted without recovery or further purification.

The following Examples are offered to further illustrate, but not limit the present invention.

EXAMPLE 1

Stability of a Peptide in the Presence of Silicon Tetrafluoride

Peptide J21-7 (H-NSSSSQFQIHGPR-OH; SEQ ID NO: 1) was synthesized on Merrifield resin using traditional peptide chemistry (Boc chemistry) with Simultaneous Multiple Peptide Synthesis (Houghten, 1985, *Proc. Natl. Acad. Sci. USA*, 82:5131–5135). The peptide was then simultaneously side-chain deprotected and cleaved from the resin with hydrogen fluoride in the presence and the absence of glass beads to verify the innocuousness of silicon tetrafluoride towards the peptide. Two different grades of commercially available grafted glass beads were used for the experiment (Aminopropyl Glass Beads 80–120 mesh, 77 μmol/g and Aminopropyl Glass Beads 200–400 mesh, 152 μmol/g Sigma Chemical Co.). Results are reported in Table 1, below.

TABLE 1

| Bag # | Content | Solids. Weight (mg) | Change in Weight. After cleavage (Δ) (mg) | Extraction with AcOH (mg) |
|---|---|---|---|---|
| M1 | Nothing | N/A | | |
|  | Total Wt. of solids in bag | zero | −10 | ~0 |
| M2 | Aminopropyl Glass beads 80–120 mesh, 77 mmol/g | 300 | | |
|  | Total Wt. of solids in bag | 300 | −310 | ~0 |
| M5 | Aminopropyl Glass beads 200–400 mesh, 152 mmol/g | 298 | | |
|  | Total Wt. of solids in bag | 298 | −292 | ~0 |
| M9 | Peptide resin J21-7 | 298 | | HPLC, MS |
|  | Total Wt. of solids in bag | 298 | −145 | 62.0 |
| M4 | Aminopropyl Glass beads 80–120 mesh, 77 mmol/g & Peptide resin J21-7 | 299 298 | | HPLC, MS |
|  | Total Wt. of solids in bag | 597 | −448 | 57.0 |
| M7 | Aminopropyl Glass beads 200–400 mesh, 152 mmol/g & Peptide resin J21-7 | 297 295 | | HPLC, MS |
|  | Total Wt. of solids in bag | 593 | −441 | 46.0 |

As is seen from Table 1 above, no weighable residue was recovered when glass beads alone are treated with HF (Table 1: Bag # M2 and M5). The weight loss of the bags during cleavage exactly corresponded to the weight of glass beads in the bags plus the weight of the HF labile protecting groups. No modification of the peptide was observed by mass spectroscopy (MS) and high pressure liwuid chromatography (HPLC) when cleaved in the presence of glass beads (Bag M9 compared to bags M4 and M7.)

EXAMPLE 2

Characterization of a Peptide Synthesized on Glass Beads

The peptide H-YGGFLR-NH$_2$ (SEQ ID NO: 2) was synthesized on two different grades of aminopropyl-grafted glass beads [Aminopropyl Glass Beads 80–120 mesh, 77 µmol/g (A) and Aminopropyl Glass Beads 200–400 mesh, 152 µmol/g (B)] using traditional peptide chemistry (Boc chemistry as in Example 1) in a small reaction vessel fitted with a fritted filter at the bottom. The peptide was then simultaneously side-chain deprotected and cleaved from the support with concomitant formation of SiF$_4$ by liquid hydrogen fluoride. Results are reported in Table 2, below.

TABLE 2

| Content | Resin Weight (mg) | Theor. Yield (mg) | Actual Yield (mg) | Molecular Weight (Calc) | (Observ.) M + H$^+$ | Δ |
|---|---|---|---|---|---|---|
| A H—YGGFLR—NH$_2$ on Aminopropyl Glass beads 80–120 mesh, 77 µeq/g | 1003 | 54.9 | 36 | 711 | 831.9 | 119.9 |
| B H—YGGFLR—NH$_2$ on Aminopropyl Glass beads 200–400 mesh, 152 µeq/g | 1006 | 108.7 | 100 | 711 | 831.9 | 119.8 |
| —CH$_2$—CH$_2$—CH$_2$—SiF$_3$: | | | | | = 127.1 | |
| —CH$_2$—CH$_2$—CH$_2$—Si(OH)$_3$: | | | | | = 121.1 | |

HPLC traces of the crude material showed the presence of the same main peak for both lots. The mass spectral analysis of the main peak observed on the HPLC trace indicates a molecular weight of 831.85. The difference of 120.85 units compared to the expected molecular weight of 711 corroborates the structure H-YGGFLR—NH—CH$_2$—CH$_2$—CH$_2$—Si(OH)$_3$ for the final compound indicating that hydrolysis of the trifluorosilyl group had occurred, although a terminal —Si(OH)$_2$F or —Si(OH)F$_2$ could also be present.

From the foregoing, it will be observed that numerous modifications and variations can be effected without departing from the true spirit and scope of the present invention. It is to be understood that no limitation with respect to the specific examples presented is intended or should be inferred. The disclosure is intended to cover by the appended claims modifications as fall within the scope of the claims.

What is claimed:

1. In a solid phase synthesis method wherein at least one reagent coupled to said solid phase support is a heterocycle, a plurality of reactions are carried out upon the solid phase-coupled heterocycle to form a solid phase-coupled reaction product and that reaction product is cleaved from the solid phase support to form a cleaved product, the improvement in which the solid phase support is converted to a volatile compound that is separated from the cleaved product by vaporization of said volatile compound, leaving behind said cleaved product.

2. The solid phase synthesis method according to claim 1 wherein said cleaved product is a heterocycle.

3. The solid phase synthesis method according to claim 1 wherein said reaction product is cleaved from said solid support and the solid phase support is converted to a volatile compound in a single step by reaction of the solid phase-coupled reaction product with hydrogen fluoride.

4. The solid phase synthesis method according to claim 1 including the further step of recovering the cleaved product.

5. The solid phase synthesis method according to claim 1 wherein said solid phase support is silica.

6. The solid phase synthesis method according to claim 5 wherein said heterocycle is coupled to said solid phase silica support by means of a linking group.

7. The solid phase synthesis method according to claim 6 wherein said silica solid support and linking group is α-chlorobenzyl $C_3$–$C_5$-alkyl-grafted glass beads.

8. The solid phase synthesis method according to claim 6 wherein said silica solid support and linking group is amino-$C_2$–$C_6$-alkyl-grafted glass beads.

* * * * *

SEQUENCE LISTING

```
<160> NUMBER OF SEQ ID NOS: 2
<210> SEQ ID NO 1
<211> LENGTH: 13
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 1

Asn Ser Ser Ser Ser Gln Phe Gln Ile His Gly Pro Arg
 1               5                  10

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 2

Tyr Gly Gly Phe Leu Arg
 1               5
```